United States Patent [19]

Brust

[11] Patent Number: 5,989,806
[45] Date of Patent: Nov. 23, 1999

[54] IMMUNODISSOCIATION FOR IMPROVING THE IMMUNOCHEMICAL DETERMINATION OF AN ANALYTE

[75] Inventor: Stefan Brust, Marburg, Germany

[73] Assignee: Behring Diagnostics GmbH, Marburg, Germany

[21] Appl. No.: 08/992,007

[22] Filed: Dec. 17, 1997

[30] Foreign Application Priority Data

Dec. 19, 1996 [DD] German Dem. Rep. .......... 196 53 074
Jan. 3, 1997 [DD] German Dem. Rep. .......... 197 00 134

[51] Int. Cl.$^6$ .................................................. G01N 33/543
[52] U.S. Cl. .............................. 435/5; 435/7.1; 435/7.92; 435/962; 435/974; 436/518
[58] Field of Search ............... 435/5, 7.1, 7.92, 435/962, 974; 436/518

[56] References Cited

U.S. PATENT DOCUMENTS 5,236,830  8/1993  Ishikawa ................................. 435/7.5
5,384,240  1/1995  Hyman et al. ............................. 435/5

FOREIGN PATENT DOCUMENTS 0 572 845 A1  12/1993  European Pat. Off. .

OTHER PUBLICATIONS

S. Hashida et al., "Detection of Antibody IgG to HIV–1 in Urine by Ultrasensitive Enzyme Immunoassay (Immune Complex Transfer Enzyme Immunoassay) Using Recombinant p24 as Antigen for Diagnosis of HIV–1 Infection", J. Clin. Lab. Analy., 8:86–95 (1994).

*Primary Examiner*—Christopher L. Chin
*Assistant Examiner*—Jennifer Graser
*Attorney, Agent, or Firm*—Finnegan, Henderson, Farabow, Garrett & Dunner, L.L.P.

[57] ABSTRACT

The present invention relates to a process for the immunochemical determination of one or more analytes in a sample using an immobilized specific receptor R1, which exhibits interactive bioaffinity with the analyte, and a specific receptor R2, which likewise exhibits interactive bioaffinity with the analyte and which as a rule is labeled. In the novel process, a receptor R3, which possesses one or more than one specific binding site for the analyte, is added and the resulting immune complexes are entirely or partially dissociated, after which they are reassociated and subsequently detected. According to a further embodiment, a receptor R4 is employed in addition to the receptor R3, which receptor R4 possesses an affinity towards R3 and is immobilized on the solid phase, with the resulting immune complexes being entirely or partially dissociated, after which they are reassociated and subsequently detected.

19 Claims, No Drawings

IMMUNODISSOCIATION FOR IMPROVING THE IMMUNOCHEMICAL DETERMINATION OF AN ANALYTE

The present invention relates to a process for the immunochemical determination of one or more analytes in a sample using an immobilized specific receptor R1, which exhibits interactive bioaffinity with the analyte, and a specific receptor R2, which likewise exhibits interactive bioaffinity with the analyte and which as a rule is labeled. In the novel process, a receptor R3, which possesses one or more than one specific binding site for the analyte, is added and the resulting immune complexes are entirely or partially dissociated, after which they are reassociated and subsequently detected. According to a further embodiment, a receptor R4 is employed in addition to the receptor R3, which receptor R4 possesses an affinity towards R3 and is immobilized on the solid phase, with the resulting immune complexes being entirely or partially dissociated, after which they are reassociated and subsequently detected.

BACKGROUND OF THE INVENTION

Customary immunological methods for diagnosing diseases which are accompanied by the formation of specific antibodies against a disease elicitor, such as viruses, bacteria, allergens, autoantigens or particular pharmaceuticals, are based on the ability of these antibodies to form complexes with antigenic structures belonging to the elicitor.

In particular embodiments of these methods, which are generally termed heterogeneous immunoassays, a sample which is to be examined for its content of, for example, specific antibodies (analyte antibodies) is brought into contact with antigenic structures of the disease elicitors, with these antigenic structures being immobilized on suitable, known support materials. Analyte antibodies which are present in the sample are bound, as an immune complex, to the antigenic structures of the disease elicitor which are immobilized on the support materials, and detected. Detection antibodies or other specific receptors (e.g. protein A) which are capable of complexing with the analyte antibody of the sample can be used for the detection.

As a rule, the detection reagent carries a label which makes it methodologically possible to detect the quantity of the antibody which is bound.

Commonly used labels are radioactive isotopes, enzymes, fluorescent, phosphorescent or luminescent substances, substances having stable unpaired electrons, latex particles, magnetic particles, metal sols and erythrocytes.

These methods are known to include both single-step and multistep detection methods. Each procedural step is customarily terminated by a separation process (washing step).

However, in heterogeneous immunoassays, the technique of the single-step method, which technique is very simple to carry out, is not suitable for detecting all disease markers. Two-step or multistep methods frequently have to be employed for technical reasons.

However, multistep methods, which are termed immunocomplex transfer enzyme immunoassays (S. Hashida et al., *Journal of Clinical Laboratory Analysis* 8:86–95 (1994)), are also known. In these methods, the entire immune complex, comprising solid phase antigen, specific antibody and labeled conjugate antigen, is detached from the solid phase. The entire immune complex is then fixed and detected after having been transferred by pipette to an antibody-binding solid phase.

While these methods are very specific, they suffer from the disadvantage that the disease elicitors to be detected or antibodies directed against them which have entered, in the first step, into a complex with the immobilized, specific receptor, can, in a reverse reaction which is known to the skilled person, in part become detached again from the complex in the subsequent reaction steps and consequently evade the detection reaction, resulting in the sensitivity, for example, being reduced.

The diagnostic efficiency of such multistep methods is reduced to a particularly great extent when the rate of the reverse reaction between the immobilized receptor and the agent to be detected is high. Such a high rate is obtained, for example, in the case of low-affinity antibodies against disease elicitors or pharmaceuticals. The skilled person knows that these effects are obtained, in particular, in the case of methods for detecting frequently mutating disease elicitors or disease markers which, following mutation, exhibit only slight interaction with the immobilized specific receptor.

EP 0 572 845 has disclosed that the reverse reaction rate is substantially reduced by adding a further receptor against structural features of the agent to be detected. This receptor has to possess more than one binding site for the agent to be detected and must not interfere with the immunochemical detection of the agent.

However, despite a marked reduction in the reverse reaction, it is likewise not possible to use this method to detect special low-affinity antibodies against disease elicitors or pharmaceuticals reliably and at high sensitivity.

The object was, therefore, to find reagents which do not have these disadvantages.

SUMMARY OF THE INVENTION

Surprisingly, it was observed that, as a result of the already formed immune complex, composed of immobilized specific receptor R1, analyte A which exhibits interactive bioaffinity with the receptor R1, and the specific receptor R2, which is directed against this analyte and which as a rule is labeled, undergoing an immunodissociation step and subsequent reassociation step, an increase in the signal can be seen when a receptor R3 is additionally added. This latter receptor reduces the proportion of analyte which is not attached to the solid phase due to the fact that it, ie. the receptor, is able to bind more than one analyte without suppressing the immune reaction between analyte A and receptor R1 one or analyte A and receptor R2.

According to another embodiment, a further immobilized receptor R4 is added in addition to R3, which receptor R4 is able to exhibit interactive bioaffinity with R3. R4 reduces the proportion of non-immobilized immune complexes by attaching the immune complex, composed of the analyte A and the receptor R3, to the solid phase. However, in this case, the specific receptor R3 does not, as in the above embodiment, have to have more than one specific binding site for the analyte A. This additional attachment of the analyte A, and consequently also of the receptor R2, which as a rule carries the label, markedly increases the signal yield and, ultimately, increases the sensitivity of the assay for the analyte A.

According to another embodiment, the receptor R4 is immobilized on a second solid phase and the dissociated immune complexes, for example R3-A-R2, are transferred from the first solid phase to the second solid phase, where the reassociation step and also the detection of R2 take place.

Within the meaning of this invention, the analyte A which is to be detected can either be an antibody which is induced, for example, by a disease elicitor or an antigen such as the disease elicitor itself.

DESCRIPTION OF THE PREFERRED EMBODIMENTS

The invention therefore relates to a process for the immunological determination of one or more analytes using:

a specific receptor R1, with this specific receptor R1 being immobilized on a support and the extent of the binding of the analyte to the specific receptor R1 being determined by means of a further specific receptor R2, which directly or indirectly carries a label, and with the process including a dissociation step, wherein a receptor R3, which possesses one or more than one binding site for the agent A to be detected, which does not possess any affinity for the immobilized specific receptor R1 and which is not labeled, is added and the extent of the binding of the analyte A to the specific receptor R2, which directly or indirectly carries a label, is determined following reassociation.

The invention also relates to a process for the immunological determination of one or more analytes using:

a specific receptor R1, with this specific receptor R1 being immobilized on a support and the extent of the binding of the analyte A to the specific receptor R1 being determined by means of a further specific receptor R2, which directly or indirectly carries a label, and with the process including a dissociation step, wherein, in addition to the binding factor R3, which in this case does not have to have more than a single binding site for the agent to be detected, a further specific immobilized or immobilizable receptor R4 is added, which receptor R4 exhibits an affinity for R3, and the extent of the binding of the analyte A to the specific receptor R2, which directly or indirectly carries a label, is determined following reassociation.

The invention furthermore relates to a process for the immunological determination of one or more analytes using:

a specific receptor R1, with this specific receptor R1 being immobilized on a support and the extent of the binding of the analyte A to the specific receptor R1 being determined by means of a further specific receptor R2, which directly or indirectly carries a label, and with the process including a dissociation step, wherein, in addition to the binding factor R3, which in this case does not have to have more than a single binding site for the agent to be detected, the dissociated immune complexes, for example R3-A-R2, are transferred to a second solid phase, which comprises a further specific immobilized or immobilizable receptor R4, which receptor R4 exhibits an affinity for R3, and the extent of the binding of the analyte A to the specific receptor R2, which directly or indirectly carries a label, is determined following reassociation.

Within the meaning of the present invention, unlabeled means that R3 either does not carry any label or at least does not carry that label which is used for determining the extent of the binding of the analyte to the specific receptor.

The processes in which the immobilized specific receptors R4 can be used are known, in all their embodiments, to the skilled person. The important factor is that the novel processes can be employed, in suitable form, in all immunochemical methods in which an immunochemical, or comparable, binding of an analyte to a, preferably immobilized, specific receptor takes place in a first step and a direct or indirect detection takes place in a second, but not necessarily chronologically separate, step.

These methods are preferably employed in the process which is known to the skilled person as sandwich ELISA, with an enzyme, preferably having a chromogenic or fluorogenic substrate, or a luminescent label preferably being used as the labeling system. However, the embodiment which is selected does not have a primary influence on the possible uses of the novel processes.

Microtitration plates, magnetic particles, latex particles or test elements having a chemical matrix, for example test modules comprising fibers or membranes, are preferably used as solid phases.

The skilled person knows that immunochemical methods, as described above, can be employed for simultaneously determining different analytes, for example HIV 1 (HIV= human immunodeficiency virus) and HIV 2, either individually or in combination with each other, or HIV 1 and/or HIV 2 in combination with HCV (hepatitis C virus or hepatitis C virus antigen). Analytes in the above-mentioned sense can be either the viral antigens or the antibodies which are directed against them. Such embodiments are also included herewith.

Within the meaning of the invention, dissociation comprises all chemical and physical methods which enable bioaffinity interactions to be disrupted or diminished in a reversible manner. The skilled person is familiar with chemical substances, such as thiocyanate, urea or guanidine, which are used in the immunochemical purification of proteins and antibodies. A dissociation can also be brought about by means of immunological methods such as competition with suitable immunologically active substances. Dissociation can furthermore be achieved by using acidic or alkaline solutions. The skilled person is likewise familiar with physical methods of dissociation: for example temperature differences, microwaves or ultrasound.

Within the meaning of the present invention, reassociation means, inter alia, bringing about non-dissociating conditions, for example by means of neutralizing or diluting or simply by means of reversing the dissociating conditions which previously prevailed, for example removing the above-mentioned temperature differences or by switching off the microwave generator or ultrasound generator.

Within the meaning of the invention, receptors R3 are specific binding partners which possess one or more than one bioaffinity binding site for the analyte A. In addition, they can enter into an interaction with the receptor R4. Binding partners or components of this receptor R3 can be conjugates of antibodies or antibodies themselves. These antibodies or antibody fragments, or conjugates thereof, can be directed against A or else also against A and R4. The receptor R3 can also comprise an antibody or antibody fragment which is coupled to a structural element against which the receptor R4 is directed.

Within the meaning of the invention, receptors R4 are specific binding partners which possess one or more bioaffinity binding sites for R3. Receptors or components of this receptor can be conjugates of antibodies/antibody fragments or antibodies/antibody fragments themselves. These antibodies/antibody fragments, or conjugates thereof, can be directed against R3 or else possess antigenic structures which are recognized by binding sites belonging to receptor R3. R4 can also comprise a protein which is coupled to a structural element against which R3 is directed.

The invention also relates to a reagent for use in the above-mentioned process.

Preferred combinations of receptors for detecting specific antigens (analyte) are:

R1: antibody which is directed against the analyte

R2: antibody which is provided with a label and which is directed against the analyte R3: antibody which is directed against the analyte A.

Preferred combinations of receptors for specific detecting antigens (analyte) are:

R1: antibody which is directed against the analyte A

R2: antibody which is provided with a label and which is directed against the analyte A R3: antibody which is directed against the analyte A R4: antibody which is directed against the antibody R3.

When antigen is being detected, an antibody or an antibody fragment which does not recognize the same epitope as does the solid-phase antibody R1 or the conjugate antibody R2 is preferably used as receptor R3.

Preferred combinations of receptors for detecting specific antibodies (analyte) are:

R1: antigen against which the analyte A is directed

R2: antigen which is provided with a label and against which the analyte A is directed R3: antibody which is directed against the analyte A.

Preferred combinations of receptors for detecting specific antibodies (analyte) are:

R1: antigen against which the analyte A is directed

R2: antigen which is provided with a label and against which the analyte A is directed R3: antibody which is directed against the analyte A R4: antibody which is directed against the antibody R3.

Particularly preferred combinations of receptors for detecting specific antibodies (analyte) are:

R1: antigen against which the analyte A is directed

R2: antigen which is provided with a label and against which the analyte A is directed R3: antibody which is directed against the analyte A and carries additional epitopes which are not antibody-intrinsic R4: antibody which is directed against an additional epitope of antibody R3, which epitope is not antibody-intrinsic.

The skilled person is familiar with methods for preparing those conjugates which in each case comprise an antibody and an additional antigen (e.g. biotin or digoxigenin) which is not antibody-intrinsic. While retaining the bioaffinity function of the starting materials, such conjugates can be prepared, for example, by means of linking, with the aid of chemical reagents, or by means of bioaffinity interaction. Hybrid molecules can also be produced by means of chemical synthesis, the hybridoma technique or recombinant DNA methods.

The novel reagent can be used in a large number of human and veterinary diagnostic methods. Examples which may be cited are two-step or multistep tests for detecting antibodies, of different immunoglobulin classes, against structural features of viruses (e.g. hepatitis A, B and C viruses and also different HIV types), bacterial and parasitic pathogens and also allergic diseases. Other examples are the detection of disease elicitors such as viruses (e.g. hepatitis B virus), bacteria, parasites and allergens, and also of disease markers (e.g. tumor markers) in multistep detection methods.

The present invention is additionally clarified by the following examples, which are not, however, intended to signify any restriction of the more general teaching, and by the patent claims.

EXAMPLE 1

1a) Preparation of the Solid Phase

Type B microtitration plates (from Nunc, Roskilde, Denmark) are incubated, at 4° C. for 24 hours, together with 100 μl per well of coating solution (600 μl recombinant gp41 [Behringwerke AG, Marburg, FRG] and 10 mg/ml monoclonal antibody against biotin [Behringwerke AG, Marburg, FRG] in 50 mM sodium carbonate buffer, pH 9.5). The wells of the microtitration plates are then washed three times with 300 μl of washing solution (50 mM Tris, 0.1% TWEEN 20, pH 7.2) on each occasion. The microtitration plates, which are dried over silica gel, are stable for about 1 year under anaerobic conditions.

1b) Preparation of the Conjugate 10 mg of HIV 1 gp41 peptide (IAF Biochem, Laval, Canada) are dissolved in 1 ml of glacial acetic acid/water (50:50, v/v). After neutralizing with 5N sodium hydroxide solution, a 10-fold molar excess of N-γ-maleimidobutyrylsuccinimide is added and the mixture is incubated at room temperature for 1 hour. The heterobifunctional reagent which has not reacted is separated off by means of gel filtration (SEPHADEX G-25) using 100 mM sodium phosphate, 5 mM nitrilotriacetic acid, pH 6.0.

10 mg of horse radish peroxidase (Boehringer Mannheim, Mannheim, FRG) are incubated, at room temperature for 1 hour, in 10 ml of 10 mM sodium phosphate, 100 mM sodium chloride, pH 8.0, together with a 100-fold molar excess of 2-iminothiolane. Free modifying reagent is then removed by means of gel filtration (SEPHADEX G-25) using 100 mM sodium phosphate, 5 mM nitrilotriacetic acid, pH 6.0.

The two eluates (SH-activated peroxidase and maleimide-modified HIV 1 peptide) are combined and incubated at room temperature over night. After the reaction has been stopped with 1/10 vol of 100 mM N-ethylmaleimide, the conjugate is freed from unreacted HIV 1 peptide by means of gel filtration (SEPHADEX G-25). After being concentrated (2 mg/ml), the conjugate is stored at −20° C.

1c) Preparation of the Biotinylated Antibody 10 mg of monoclonal antibody against human immunoglobulin G (Behringwerke AG, Marburg, FRG), dissolved in 10 mM sodium phosphate, 100 mM sodium chloride, pH 8.0, are incubated, at room temperature for 1 hour together with a 10-fold molar excess of N-hydroxysuccinimide-X-biotin, dissolved in 10 ml of 10 mM sodium phosphate, 100 mM sodium chloride, pH 8.0. Free modifying reagent is then removed by means of gel filtration (SEPHADEX G-25) using 100 mM Tris, 5 mM nitrilotriacetic acid, pH 7.0.

EXAMPLE 2

Use of the Novel Reagent

2a) Enzyme Immnunoassay for Detecting HIV 1 Antibodies (Reference System I)

An enzyme immunoassay for detecting anti-HIV 1 is carried out as follows:

25 μl of sample buffer (0.3 M Tris/HCl, 1% albumin, 2% TWEEN 20, pH 7.2) are incubated, at 37° C. for 30 minutes, together with 100 μl of human serum in the wells of the microtitration plates prepared as described in Example 1a. After the plates have been washed 4 times in 50 mM PBS, 0.1% TWEEN 20, 125 μl of the conjugate prepared as described in Example 1b (diluted 1:1000 in 0.1 M Tris/HCl, 1 mM glycine, 0.2% albumin, 0.4% PLURONIC F64, 1 mg/l monoclonal antibodies against human immunoglobulin G, pH 8.1) are pipetted into each well. The 30-minute incubation (+37° C.) is terminated with a further 4 washing steps. The bound peroxidase activity, which correlates directly with the number of bound anti-HIV 1 antibodies, is determined by adding $H_2O_2$/tetra-methylbenzidine. After 30 minutes at room temperature, substrate conversion is stopped by adding 0.5 M sulfuric acid. The extinction is determined at 450 nm.

2b) Enzyme Immunoassay for Detecting HIV 1 Antibodies (Novel System I)

An enzyme immunoassay for detecting anti-HIV 1 is carried out as follows:

25 $\mu$l of sample buffer (0.3 M Tris/HCl, 1% albumin, 2% TWEEN 20, pH 7.2) are incubated, at 37° C. for 30 minutes, together with 100 $\mu$l of human serum in the wells of the microtitration plates prepared as described in Example 1a. After the plates have been washed 4 times with 50 mM PBS, 0.1% TWEEN 20, 100 $\mu$l of the dissociation buffer (5 mM glycine/HCl, pH 2.5) are added at RT for 30 min. 25 $\mu$l of the conjugate prepared as described in Example 1b (diluted 1:200 in 0.5 M Tris/HCl, 1 albumin, 2% PLURONIC F64, 5 mg/l monoclonal antibody against human immunoglobulin G, pH 8.1) are then pipetted into each well without any washing step. The 30-minute incubation (+37° C.) is terminated with a further 4 washing steps. The bound peroxidase activity, which correlates directly with the number of bound anti-HIV 1 antibodies, is determined by adding $H_2O_2$/tetramethylbenzidine. After 30 minutes at room temperature, substrate conversion is stopped by adding 0.5 M sulfuric acid. The extinction is determined at 450 nm.

Anti-HIV 1-positive samples and also anti-HIV 1-positive samples having an unusually low reactivity, and anti-HIV-negative sera, were investigated both in the reference system and in the novel enzyme immunoassay.

The results (extinction units) of the investigation are given in Table 1.

TABLE 1

| Sample designation | Anti-HIV status | Dilution | Comment | Reference system I | Novel system I |
|---|---|---|---|---|---|
| Negative control | Negative | Native | | 0.098 | 0.103 |
| Positive control | Positive | 1:4000 | High affinity | 1.575 | 1.412 |
| 9111/39 | Positive | 1:100 | low affinity | 1.211 | 1.653 |
| 9111/39 | Positive | 1:200 | low affinity | 0.520 | 0.886 |
| 9111/46 | Positive | 1:50 | low affinity | 0.528 | 0.927 |
| 9111/46 | Positive | 1:100 | low affinity | 0.310 | 0.489 |
| 9205/19 | Positive | 1:8000 | high affinity | 0.906 | 0.877 |
| BS 1-5 | Negative | Native | | 0.076 | 0.089 |
| BS 1-17 | Negative | Native | | 0.077 | 0.078 |
| BB 1-33 | Negative | Native | | 0.090 | 0.075 |
| BS 1-59 | Negative | Native | | 0.083 | 0.091 |

Marked differences can be seen in the signal produced in the two test systems, particularly in the case of low-affinity samples (e.g. 9111/46). Sensitivity with regard to these samples is almost doubled in comparison with the reference system I. Samples having a high affinity for the coating antigen, and which are already recognized at high dilution in the reference system I, do not show any increased signal in the novel system I. Anti-HIV-negative sera react in a comparable manner in the two test systems.

EXAMPLE 3

Use of the Novel Reagent

3a) Enzyme Immunoassay for Detecting HIV 1 Antibodies (Reference System II)

An enzyme immunoassay for detecting anti-HIV 1 is carried out as follows:

25 $\mu$l of sample buffer (0.3 M Tris/HCl, 1% albumin, 2% TWEEN 20, pH 7.2) are incubated, at 37° C. for 30 minutes, together with 100 $\mu$l of human serum in the wells of the microtitration plates prepared as described in Example 1a. After the plates have been washed 4 times with 50 mM PBS, 0.1% TWEEN 20, 125 $\mu$l of the conjugate prepared as described in Example 1b (diluted 1:1000 in 0.1 M Tris/HCl 1 mM glycine, 0.2% albumin, 0.4% PLURONIC F64, 1 mg/l monoclonal antibody against human immunoglobulin G, which monoclonal antibody has been biotinylated as described in Example 1c), pH 8.1) are pipetted into each well. The 30-minute incubation (+37° C.) is terminated with a further 4 washing steps. The bound peroxidase activity, which correlates directly with the number of bound anti-HIV 1 antibodies, is determined by adding $H_2O_2$/tetramethylbenzidine. After 30 minutes at room temperature, substrate conversion is stopped by adding 0.5 M sulfuric acid. The extinction is determined at 450 nm.

3b) Enzyme Immunoassay for Detecting HIV 1 Antibodies (Novel System II)

An enzyme inmmunoassay for detecting anti-HIV 1 is carried out as follows:

25 $\mu$l of sample buffer (0.3 M Tris/HCl, 1% albumin, 2% TWEEN 20, pH 7.2) are incubated, at 37° C. for 30 minutes, together with 100 $\mu$l of human serum in the wells of the microtitration plates prepared as described in Example 1a. After the plates have been washed 4 times with 50 mM PBS, 0.1% TWEEN 20, 100 $\mu$l of the dissociation buffer (5 mM glycine/HCl, pH 2.5) are added at RT for 30 min. 25 m$\mu$l of the conjugate prepared as described in Example 1b (diluted 1:200 in 0.5 M Tris/HCl, 1% albumin, 2% PLURONIC F64, 5 mg/l monoclonal antibody against human immunoglobulin G, which monoclonal antibody has been biotinylated as described in Example 1c), pH 8.1) are then pipetted into each well without any washing step. The 30-minute incubation (+37° C.) is terminated with a further 4 washing steps. The bound peroxidase activity, which correlates directly with the number of bound anti-HIV 1 antibodies, is determined by adding $H_2O_2$/tetra-methylbenzidine. After 30 minutes at room temperature, substrate conversion is stopped by adding 0.5 M sulfuric acid. The extinction is determined at 450 nm.

Anti-HIV 1-positive samples and also anti-HIV 1-positive samples having an unusually low reactivity, and anti-HIV-negative sera, were investigated both in the reference system and in the novel enzyme immunoassay.

The results (extinction units) of the investigation are given in Table 2.

TABLE 2

| Sample designation | Anti-HIV status | Dilution | Comment | Reference system II | Novel system II |
|---|---|---|---|---|---|
| Negative control | Negative | Native | | 0.149 | 0.140 |
| Positive control | Positive | 1:800 | High affinity | 0.997 | 1.834 |
| 9111/39 | Positive | 1:100 | low affinity | 1.813 | >2.500 |
| 9111/39 | Positive | 1:200 | low affinity | 0.988 | 1.714 |
| 9111/46 | Positive | 1:50 | low affinity | 0.694 | 0.800 |
| 9111/46 | Positive | 1:100 | low affinity | 0.341 | 0.502 |
| 9205/19 | positive | 1:8000 | high affinity | 0.997 | 1.834 |
| BS 1-5 | Negative | Native | | 0.098 | 0.090 |
| BS 1-17 | Negative | Native | | 0.086 | 0.086 |
| BS 1-33 | Negative | Native | | 0.089 | 0.080 |
| BS 1-59 | Negative | Native | | 0.084 | 0.079 |

Marked differences can be seen in the signal produced in the two test systems, particularly in the case of low-affinity samples (e.g. 9111/39). Sensitivity with regard to these samples is doubled in comparison with the reference system II. Samples having a high affinity for the coating antigen, and which are already recognized at high dilution in the reference system II, give a further increase in signal in the novel system II. Anti-HIV-negative sera react in a comparable manner in the two test systems.

I claim:

1. A process for determining an analyte A, which comprises:
   (a) immobilizing on a solid phase, a receptor R1 having a binding affinity for analyte A;
   (b) bringing a sample, which may contain analyte A, into contact with a receptor R1 to form an immune complex R1-A;
   (c) carrying out one or more washing steps;
   (d) adding sequentially, in either order, or adding simultaneously, a labeled receptor R2 having at least one binding site specific for the analyte A, and an unlabeled receptor R3 having more than one binding site specific for analyte A;
   (e) exposing the immune complexes formed to a dissociating condition and then to a non-dissociating condition, which leads to reassociation and formation of an immobilized immune complex comprising analyte A, R1, R2, and R3; and
   (f) determining the quantity of analyte A immobilized on the solid phase by measuring the quantity of labeled receptor present.

2. The process as claimed in claim 1, wherein in step (a), a receptor R4 is co-immobilized on the solid phase, said receptor R4 having at least one binding site specific for the receptor R3; and wherein the receptor R3 has at least one binding site specific for analyte A; and wherein the immobilized immune complex formed in step (e) comprises analyte A, R1, R2, and R3 or analyte A, R4, R2, and R3.

3. A process for determining an analyte A, which comprises:
   (a) immobilizing on a solid phase, a receptor R1 having a binding affinity for analyte A;
   (b) bringing a sample, which may contain analyte A, into contact with a receptor R1 to form an immune complex R1-A;
   (c) carrying out one or more washing steps;
   (d) dissociating the immune complex R1-A;
   (e) adding sequentially, in either order, or adding simultaneously, a labeled receptor R2 having at least one binding site specific for the analyte A, and an unlabeled receptor R3 having more than one binding site specific for analyte A, under non-dissociating conditions to allow reassociation and formation of immune complexes;
   (f) bringing the immune complexes of step (f) in contact with a second solid phase on which a receptor R4 having a binding affinity for receptor R3 is immobilized, which leads to the formation of immobilized immune complexes comprising analyte A, R1, R2, R3, and R4; and
   (g) determining the quantity of analyte A immobilized on the solid phases by measuring the quantity of labeled receptor present.

4. The process as claimed in claim 1, wherein
   R1 and R3 are antibodies, or antibody fragments, having a binding affinity for the analyte A; and
   R2 is a labeled antibody, or labeled antibody fragment, having a binding affinity for the analyte A.

5. The process as claimed in claim 2, wherein
   R1 and R3 are antibodies, or antibody fragments, having a binding affinity for the analyte A;
   R2 is a labeled antibody, or labeled antibody fragment, having a binding affinity for the analyte A; and
   R4 is an antibody, or antibody fragment, having a binding affinity for R3.

6. The process as claimed in claim 5, wherein R3 has a binding affinity for an epitope that is different from the epitope for which R1 or R2 have a binding affinity.

7. The process as claimed in claim 1, wherein the analyte A is an antibody,
   R1 is an antigen for which the analyte A has a binding affinity;
   R2 is a labeled antigen for which the analyte A has a binding affinity; and
   R3 is an antibody, or antibody fragment, having a binding affinity for the analyte A.

8. The process as claimed in claim 2, wherein the analyte A is an antibody;
   R1 is an antigen for which the analyte A has a binding affinity;
   R2 is a labeled antigen for which the analyte A has a binding affinity;
   R3 is an antibody, or antibody fragment, having a binding affinity for the analyte A; and
   R4 is an antibody, or antibody fragment, having a binding affinity for R3.

9. The process as claimed in claim 8, wherein
   R3 has an additional epitope, wherein said epitope is not antibody-directed; and
   R4 has a binding affinity for the additional epitope of R3.

10. The process as claimed in claim 3, wherein
    R1 and R3 are antibodies, or antibody fragments, having a binding affinity for the analyte A;
    R2 is a labeled antibody, or labeled antibody fragment, having a binding affinity for the analyte A; and
    R4 is an antibody, or an antibody fragment, having a binding affinity for R3.

11. The process as claimed in claim 10, wherein R3 has a binding affinity for an epitope that is different from the epitope for which R1 or R2 have a binding affinity.

12. The process as claimed in claim 3, wherein Analyte A is an antibody;
    R1 is an antigen for which the analyte A has a binding affinity;
    R2 is a labeled antigen for which the analyte A has a binding affinity;
    R3 is an antibody, or antibody fragment, having a binding affinity for the analyte A; and
    R4 is an antibody, or antibody fragment, having a binding affinity for R3.

13. The process as claimed in claim 12, wherein
    R3 has an additional epitope, wherein said epitope is not antibody-directed; and
    R4 has a binding affinity for the additional epitope of R3.

14. The process as claimed in claim 1, wherein the analyte A to be determined is an antibody having a binding affinity for an antigenic component of a human immunodeficiency virus (HIV), an antigenic component of a HIV, an antibody having a binding affinity for an antigenic component of a hepatitis virus, an antibody having a binding affinity for a bacterial pathogen, an antibody having a binding affinity for a parasitic pathogen, an antigenic component of a hepatitis virus, an allergen, or a tumor marker.

15. The process as claimed in claim 14, wherein the analyte A is an antibody having a binding affinity for the antigenic component of a human immunodeficiency virus (HIV).

16. The process as claimed in claim 3, wherein the analyte A to be determined is an antibody having a binding affinity for an antigenic component of a human immunodeficiency virus (HIV), an antigenic component of an HIV, an antibody having a binding affinity for an antigenic component of a hepatitis virus, an antibody having a binding affinity for a bacterial pathogen, an antibody a binding affinity for a parasitic pathogen, an antigenic component of a hepatitis virus, an allergen, or a tumor marker.

17. The process as claimed in claim 16, wherein the analyte A is an antibody having a binding affinity for the antigenic component of a human immunodeficiency virus (HIV).

18. The process as claimed in claim 1, wherein the dissociation step of step (e) comprises an immunological method, a temperature difference, microwaves, adding a chemical substance, or ultrasound.

19. The process as claimed in claim 18, wherein the chemical substance is selected from thiocyanate, urea, guanidine, an acidic solution, and a basic solution.

\* \* \* \* \*

UNITED STATES PATENT AND TRADEMARK OFFICE
CERTIFICATE OF CORRECTION

PATENT NO. : 5,989,806
DATED : November 23, 1999
INVENTOR(S) : Brust

It is certified that error appears in the above-identified patent and that said Letters Patent is hereby corrected as shown below:

Claim 16, column 11, line 10, after "antibody", insert --having--.

Signed and Sealed this

Seventh Day of November, 2000

Attest:

Q. TODD DICKINSON

*Attesting Officer*          *Director of Patents and Trademarks*